United States Patent [19]
Majuri

[11] Patent Number: 5,919,419
[45] Date of Patent: *Jul. 6, 1999

[54] ANALYZER CUVETTE, METHOD AND DIAGNOSTIC TEST KIT FOR DETERMINATION OF ANALYTES IN WHOLE BLOOD SAMPLES

[75] Inventor: Raimo Majuri, Espoo, Finland

[73] Assignee: Orion-yhtymä Oy, Espoo, Finland

[*] Notice: This patent issued on a continued prosecution application filed under 37 CFR 1.53(d), and is subject to the twenty year patent term provisions of 35 U.S.C. 154(a)(2).

[21] Appl. No.: 08/696,996

[22] PCT Filed: Feb. 17, 1995

[86] PCT No.: PCT/FI95/00081

§ 371 Date: Oct. 9, 1996

§ 102(e) Date: Oct. 9, 1996

[87] PCT Pub. No.: WO95/22764

PCT Pub. Date: Aug. 24, 1995

[30] Foreign Application Priority Data

Feb. 22, 1994 [FI] Finland .................................. 940823

[51] Int. Cl.⁶ .................................................. B01D 21/26
[52] U.S. Cl. .............................. 422/101; 422/57; 422/61; 422/68.1; 422/73; 422/102; 436/18; 210/789
[58] Field of Search ................................ 422/57, 58, 60, 422/61, 68.1, 72, 73, 101, 102; 436/18; 210/516, 789

[56] References Cited

U.S. PATENT DOCUMENTS

| | | | |
|---|---|---|---|
| 3,713,775 | 1/1973 | Schmitz | 23/253 R |
| 3,902,964 | 9/1975 | Greenspan | 195/1 |
| 4,397,897 | 8/1983 | Schulke | 428/35 |
| 4,675,159 | 6/1987 | Al-Sioufi | 422/36 |
| 4,770,779 | 9/1988 | Ichikawa et al. | 210/516 |
| 4,816,168 | 3/1989 | Carrol et al. | 210/782 |
| 5,051,239 | 9/1991 | Von Der Goltz | 422/73 |
| 5,213,765 | 5/1993 | Kasai et al. | 422/101 |
| 5,246,666 | 9/1993 | Vogler et al. | 422/73 |
| 5,257,633 | 11/1993 | Vogler et al. | 128/763 |
| 5,262,067 | 11/1993 | Wilk et al. | 210/767 |
| 5,296,192 | 3/1994 | Carroll et al. | 422/56 |
| 5,326,535 | 7/1994 | Vogler et al. | 422/102 |
| 5,344,611 | 9/1994 | Vogler et al. | 422/101 |
| 5,378,431 | 1/1995 | Vogler et al. | 422/73 |
| 5,460,974 | 10/1995 | Kozak et al. | 436/71 |
| 5,489,386 | 2/1996 | Saunders | 210/514 |
| 5,511,558 | 4/1996 | Shepard et al. | 128/760 |
| 5,533,518 | 7/1996 | Vogler | 128/760 |
| 5,543,048 | 8/1996 | Vogler et al. | 210/513 |

FOREIGN PATENT DOCUMENTS

| | | |
|---|---|---|
| 2-21654 | 8/1988 | Australia . |
| 0 057110 | 1/1981 | European Pat. Off. . |
| 0 295526 | 6/1987 | European Pat. Off. . |
| 0-305803 | 8/1988 | European Pat. Off. . |
| 0 392377 | 4/1990 | European Pat. Off. . |
| 1498577 | 6/1963 | Germany . |
| 2-038722 | 8/1970 | Germany . |

OTHER PUBLICATIONS

Kundu et al., Description of an In Vitro Platelet Function Analyzer–PFA–100, Seminars in Thrombosis and Hemostasis, vol. 21, Suppl. 2, Feb. 1995.

Mammen et al., Preliminary Data from a Field Trial of the PFA–100 System, Seminars in Thrombosis and Hemostasis, vol. 21, Suppl. 2, Feb. 1995.

*Primary Examiner*—Harold Y. Pyon
*Attorney, Agent, or Firm*—Birch, Stewart, Kolasch & Birch, LLP

[57] ABSTRACT

The present invention relates to a specific cuvette, an assay method and a diagnostic test kit where samples of whole blood can be used for quantitative diagnostic testing without need for centrifugation, even though the blood components to be analyzed are in the plasma fraction. Using the method of the present invention the blood sample is converted into a plasma fraction and a cell fraction by shaking in a cuvette in the presence of a special agglutinating reagent A plasma fraction is obtained which is suitable to be used in diagnostic tests using immunometric or colormetric methods or test strips without physically removing the blood cells from the sample.

17 Claims, 5 Drawing Sheets

1 = PROJECTION LINE
2 = DRY BSR-REAGENT 1 2 3 4 5 6 7 8

ANALYZER CUVETTE, METHOD AND DIAGNOSTIC TEST KIT FOR DETERMINATION OF ANALYTES IN WHOLE BLOOD SAMPLES

This application is a 371 of PCT/FI95/00081 filed Feb. 17, 1995.

FIELD OF THE INVENTION

The present invention relates to a specific cuvette, an assay method and a diagnostic test kit where samples of whole blood can be used for quantitative diagnostic testing without a need for centrifugation, even though the blood components to be analyzed are in the plasma fraction. Using the method of this invention the blood sample is converted into a plasma fraction and a cell fraction by shaking in a cuvette in the presence of a special agglutinating reagent. The procedure results in the avoidance of the disturbing effect of the cell fraction which forms a solid phase. A plasma fraction is obtained which is suitable to be used in diagnostic tests using immunometric or calorimetric methods or strip tests without physically removing the blood cells from the sample.

BACKGROUND OF THE INVENTION

SEPARATION OF PLASMA COMPONENTS FROM BLOOD CELLS

Various diagnostic methods are based on the determination of the concentration of analytes in blood plasma. Often, however, the blood cells seriously disturb the assay procedure chosen and therefore it is necessary to separate the blood cells from the plasma prior to the measurement. In most cases plasma is separated by centrifugation. Although centrifugation is considered to be a routine method a device and tubes are required affecting the level of test costs. Moreover, centrifugation is a laborious step to perform. Furthermore, test tubes broken and aerosoles produced during centrifugation cause a risk of infection for the laboratory personnel.

Filtration methods are also used in some degree. However, their volumetric capacity is very low and they can be performed most satisfactorily in special applications like immunochromatography.

Methods for separation of plasma from blood components using agglutination (DE 2038722, DE 1498577) or agglutination-filtration (EP-183991 A1, EP-045476 A1, EP-0194502 B1) have been disclosed earlier. Said methods or devices are intended for narrow-segmented special applications, either as a primary plasma separation method, where the separated plasma is physically transferred into another tube or cuvette for analysis or transported by capillary forces into another membrane layer or device chamber. The purpose of these methods differ from the purposes presented in this invention. Both the production methods and the methods of use of the agglutinating component are different from those disclosed in this invention.

According to the literature potato (*Solanum tuberosum*) contains STA-lectin (*Solanum tuberosum* agglutinin) and various other carbohydrate binding proteins, which have not been completely characterized so far (Kilpatrick, D. C., Biochem. J. 1980, 191:273–275; Allen, A. K. and Neuberger, A., Biochem. J. 1973, 135:307–314; Matsumoto, I. et al., J. Biol. Chem. 1983, 258:2886–2891; Millar, D. J. et al., Biochem. J. 1992, 283:813–821). Carbohydrate binding proteins isolated from other plants and those produced by means of recombinant technology and genetic engineering may also be used. It is of importance that irrespective of the production procedure, the carbohydrate binding proteins produced all bind blood cells but not plasma glycoproteins.

The STA-lectin binds to blood cell surface antigens of various animal species, including human. The agglutination procedure is based on the binding of polyvalent lectin to cell surface carbohydrate moieties of the blood group antigens. The STA-lectin is specific for N-acetyl-D-glucosamine-oligomers but shows only minor affinity to N-acetyl-D-glucosamine-monomers or other sugar monomers or polymers.

SUMMARY OF THE INVENTION

The present invention relates to the use of an analyzer cuvette or tube, and to a method in which samples of whole blood drawn for analysis of an analyte is processed in said cuvette. The method renders it possible to analyze plasma analytes of whole blood without the disturbing effect of the cell fraction or thrombocytes. The analyzer cuvette can also be used as the primary tube for sampling small blood samples.

In the present invention the blood cells are precipitated with a reagent comprising agglutinin extracted from potato and combined to other components in strictly defined concentrations, depending on the application in use. This blood separating reagent, BSR-reagent, is then coated onto the inner surface of the analyzer cuvette or in a separate porous membrane which is either a mobile or immobile part of the analyzer cuvette or the blood sampler tube.

The inner surface of the analyzer cuvette is coated in a manner where the blood sample is, when contacted with the coated surface, converted into a plasma fraction and cell fraction, the latter forming a solid phase by the effect of the coated surface of the cuvette in addition to a slight agitation.

Moreover, the present invention provides a test kit that employs cuvettes or tubes coated with a dried reagent, preferably BSR-reagent, comprising agglutinin extracted from potato, for immunometric and calorimetric, e.g. turbidimetric or nephelometric determination of analytes in whole blood samples.

DETAILED DESCRIPTION OF THE INVENTION

Figure 1:
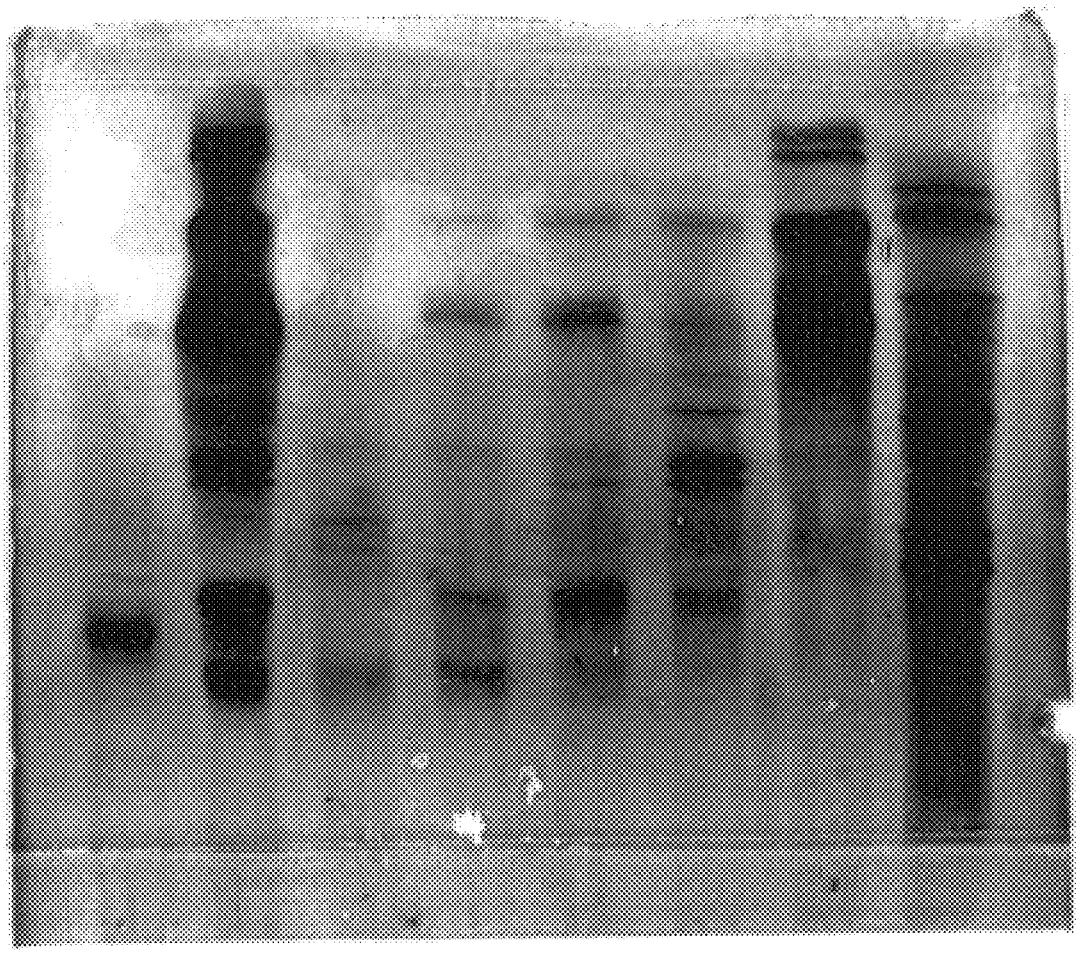
FIG. 1 shows a SDS-PAGE run on 8–25% gel (Laemmli). Samples: 1. STA-lectin (Sigma, Lot. 38F-3964), 2. BSR (UA001), 3. HPLC FR1, 4. HPLC FR2, 5. HPLC FR3, 6. HPLC FR4, 7. HPLC FR5, 8. LMW (Pharmacia)

The present invention provides a highly effective method for determining analytes in whole blood avoiding the disturbing effect of blood cells. The determination can be done directly from whole blood instead of using prior art methods where plasma/serum samples are used after premanipulation of the whole blood sample.

The agglutinating reagent of the present invention used in precipitating the blood cells comprises preferably an agglutinin extracted from potatoes. The primary, impure preparation extracted from potatoes was named "blood separating reagent" (BSR). BSR can be used in the method of the invention at different degrees of purity depending on the application used. For the purposes of the present invention the final, pure product which is prepared by diluting the primary product BSR with a suitable buffer matrix as described hereinafter, is called "BSR-reagent".

In this specification the analyzer cuvette or tube coated with the BSR-reagent is called "BSR-reagent cuvette" or "BSR-reagent tube". The cuvettes and tubes as well as the method are particularly applicable for use with small volumes of blood. The optimal blood volume is from 1 to 100 µl.

According to the method used the agglutinating BSR-reagent is dried under strictly defined conditions onto the inner surface of the blood sampler tube/analyzer cuvette or into an mobile or immobile porous membrane disk inside the analyzer cuvette. The BSR-reagent is dissolved from the surface or membrane by the effect of the liquid sample. The dried BSR-reagent is a very stable precipitating reagent, and a fast precipitation of blood cells is effected. Of importance is that the BSR-reagent does not hemolyze the cells.

The new approach of the present method is to convert the blood sample into two phases, a solid cell phase and a liquid plasma phase in the analyzer cuvette without centrifugation. The method of this invention makes it possible to avoid broken tubes and aerosoles produced during centrifugation, which may cause a risk of infection. The phase separation method disclosed for separation of blood samples is very simple. It is not dependent on any special devices and makes it possible to use whole blood as a sample. Characteristic for the present invention is that the blood cells form a solid phase which does not interfere with the assay and therefore no physical separation is required. The cell pellet obtained can remain free in the cuvette during the assay. This renders possible a rapid diffusion of plasma components due to the short diffusion distance (<0.1 mm). One very prominent advantage of the method is associated with the safety of the person handling the sample. All the infective components of the sample remain in the analyzer cuvette after the determination has been performed. After measurement the cuvette can be sealed tightly with a cap, whereby all infective components of the sample are easily disposed simultaneously without causing any risk of infection. Another prominent advantage, compared to earlier methods, is that the determination of new analytes would become possible especially from micro blood samples drawn from the finger tip. According to the method of the present invention the plasma need not be transferred into another chamber, tube or cuvette, which simplifies the function of the analyzer cuvette.

It is an object of the present invention to further exploit the capacity of agglutinins to agglutinate blood cells and to provide a method and test kit for simple and rapid assay of analytes in whole blood without the disturbing effect of blood cells.

Hereinafter, the invention is illustrated in detail by referring to the enclosed drawings. The CRP assays described in Examples 3 and 4 are merely given as examples of assay methods in which the cuvettes of the invention can be used.

PREPARATION AND CHARACTERIZATION OF THE BSR

BSR is extracted from potatoes by a method where the water soluble components are separated by pressing the potatoes to juice and by concentrating the active components (BSR) with 60% ammonium sulphate. Finally BSR is dialyzed against water and freeze dried.

The BSR is then diluted with buffer matrix containing Tris-HCl, Tris-base, Na-chloride, Na-azide and BSA in accurately defined concentrations to obtain the BSR-reagent, said concentrations varying for different applications and being dependent on the volume of the dried reagent. The reagent is dried onto the inner wall of an analyzer cuvette or into a porous membrane. However, the active reagent is not immobilized but is dissolved by the effect of the liquid sample.

Figure 2:
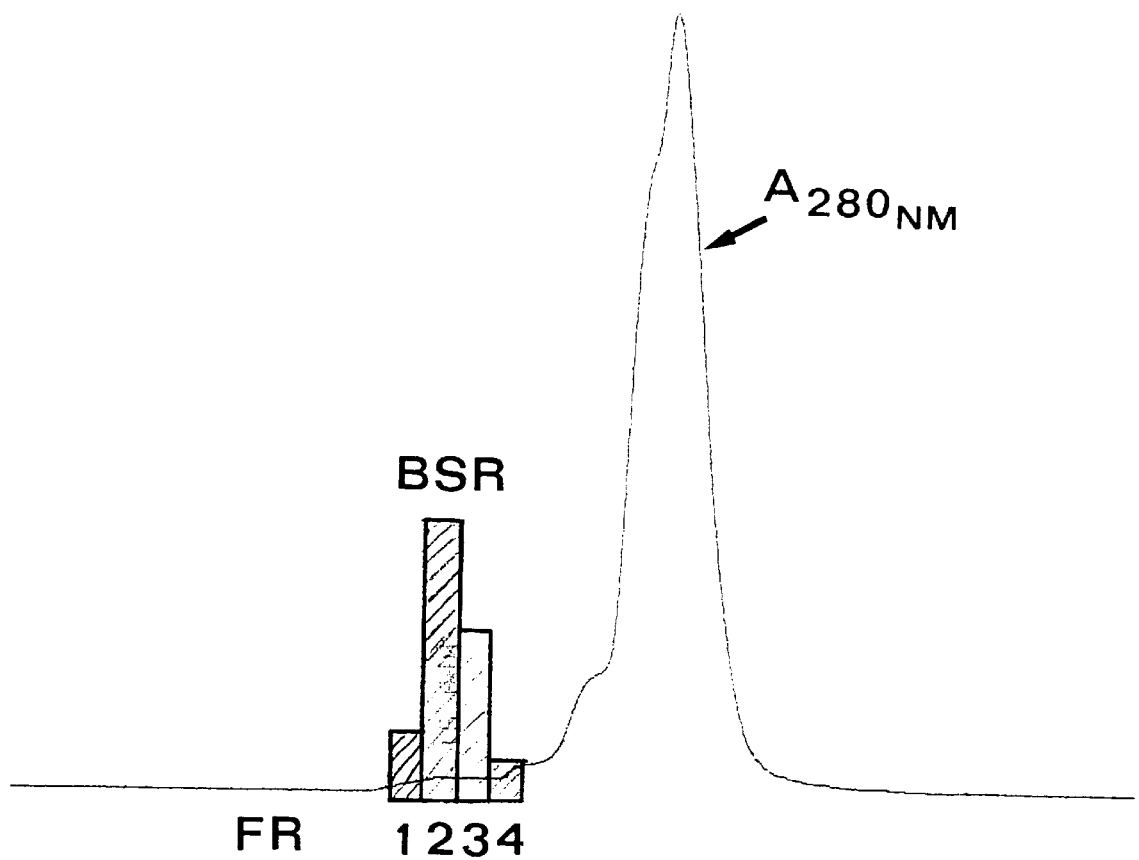
FIG. 2 shows a HPLC-run of a BSR-sample (Lot. UA001) using a G3000SW×1 column. The detection is performed at a wavelength of 280 nm. The active component of the fraction was measured by means of an agglutination test.

The protein composition of the BSR has been analyzed by means of HPLC-methods. FIG. 1 shows a SDS-PAGE run on 8–25% gel (Laemmli). Samples: 1. STA-lectin (Sigma, Lot. 38F-3964), 2. BSR-sample (UA001), 3. HPLC FR1, 4. HPLC FR2, 5. HPLC FR3, 6. HPLC FR4, 7. HPLC FR5, 8. LMW (Pharmacia). FIG. 2 shows a HPLC-run of a BSR-sample (Lot. UA001) using a G3000SW×1 column. The detection is performed at a wavelength of 280 nm. The active component of the fraction was measured by means of an agglutination test.

The molecular weight (180 kd) of the active component of the BSR was larger than that of the molecular weight of the main component (160 kd) of the STA-lectin (Sigma, L-4266, lot. 38F-3864). The mobility of the STA-lectin (Sigma) on a SDS-PAGE gel was different, corresponding to a molecular weight of 120 kd, whereas it was found to be 180 kd for the active component of BSR. Ninety-eight (98) % of the BSR-protein composition consisted of the kd 15 and kd 32 proteins.

TABLE 1

The competitive inhibition of BSR-reagent by N,N',N"-triacetylchitotriose.

| CHITOTRIOSE (µg) | AGGREGATION | PRECIPITATION |
| --- | --- | --- |
| 0 | +++ | + |
| 50 | ++ | + |
| 100 | + | − |
| 150 | ± | − |
| 200 | − | − |
| 250 | − | − |

To perform the assay we used BSR-reagent cuvettes intended for the Quikread 3 analyzer into which 350 µg of BSR-reagent has been dried. Thereafter, 50 µl chitotriose followed by 20 µl of EDTA-blood were pipetted into the cuvettes. The agglutination of cells was studied visually. The result shows that the behaviour of the BSR-reagent was identical with that of the STA-lectin.

STABILITY

Table 2 summarizes the stability data of BSR-reagent cuvettes at different temperatures. The shelf life was studied by means of BSR-reagent cuvettes intended for the Quikread 3 CRP test. The agglutination was tested by pipetting 20 µl of EDTA-blood into BSR-reagent cuvettes. As a result the blood cells were precipitated by means of the BSR-reagent coated onto the inner walls of the cuvettes whereafter 1 ml of buffer was added. The absorbance value was measured with Quikread 3 analyzer.

TABLE 2

| TEMPERATURE (°C.) | TIME | ACTIVITY |
| --- | --- | --- |
| +4 | >12 months | +++ |
| R.T. | >12 months | +++ |
| +37 | >12 months | +++ |
| +50 | >7 hours | +++ |
| +75 | >7 hours | +++ |
| +100 | >30 minutes | +++ |

BSR-REAGENT CUVETTES FOR QUIKREAD 3 ANALYZER.

BSR-reagent was produced by dissolving 500 mg of lyophilized BSR (UA001), 87.5 ml of distilled water and 12.5 ml of buffer. Fifty (50) µl of the reagent were applied into round-bottom acrylic cuvettes of Quikread 3 analyzer and dried at room temperature.

Figure 3:
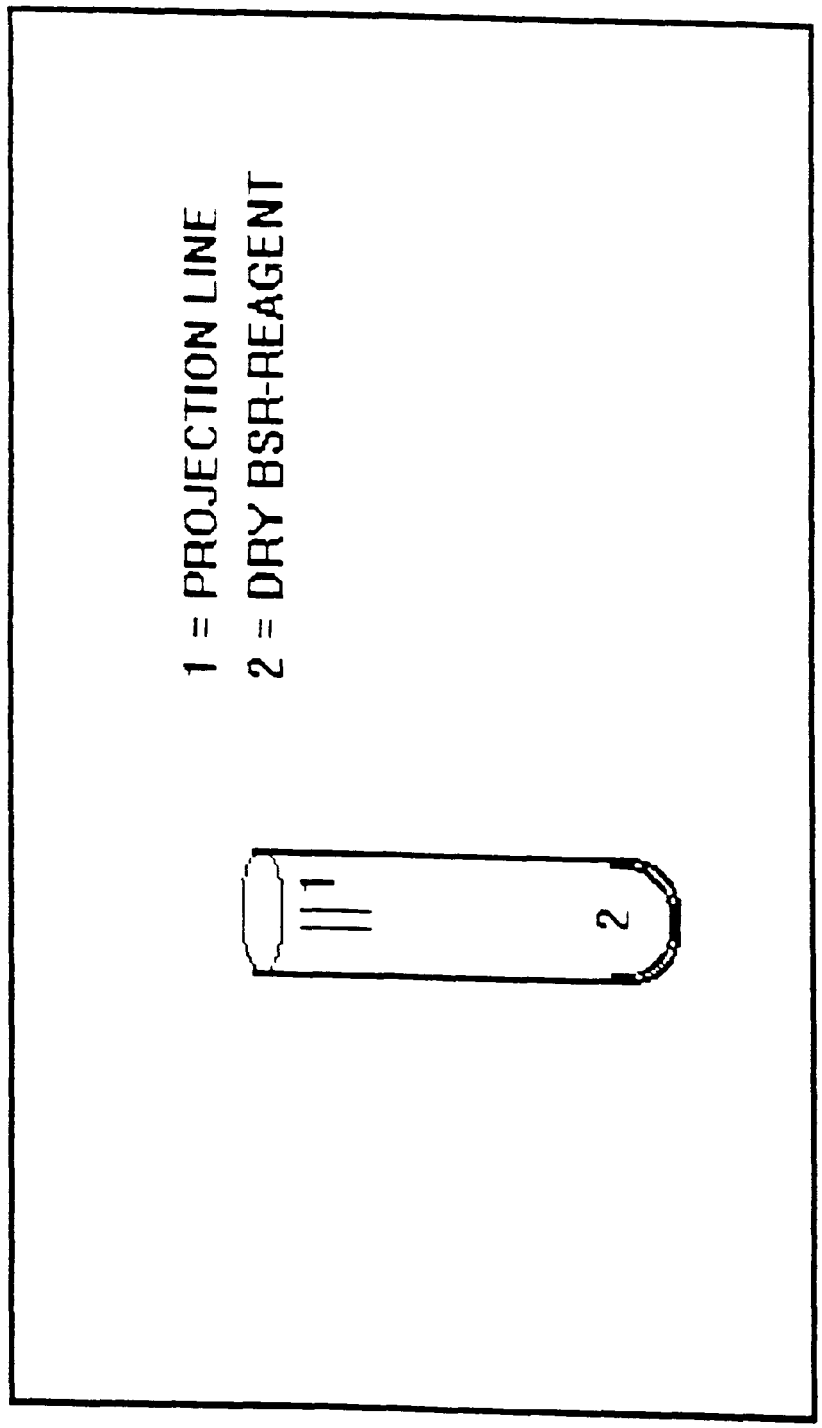
FIG. 3 shows an acrylic analyzer cuvette, intended to be used specifically with Quikread 3 analyzer, composed of a projection line (1) and the BSR-reagent (2) dried onto the inner wall of the tube useful in practising the present invention.

FIG. 3 shows the tube used with Quikread 3 analyzer containing a projection line (1) and the BSR-reagent (2) dried onto the wall of the tube.

BSR-REAGENT CUVETTES CONTAINING A MEMBRANE DISK FOR QUIKREAD ANALYZER 3

Figure 4:
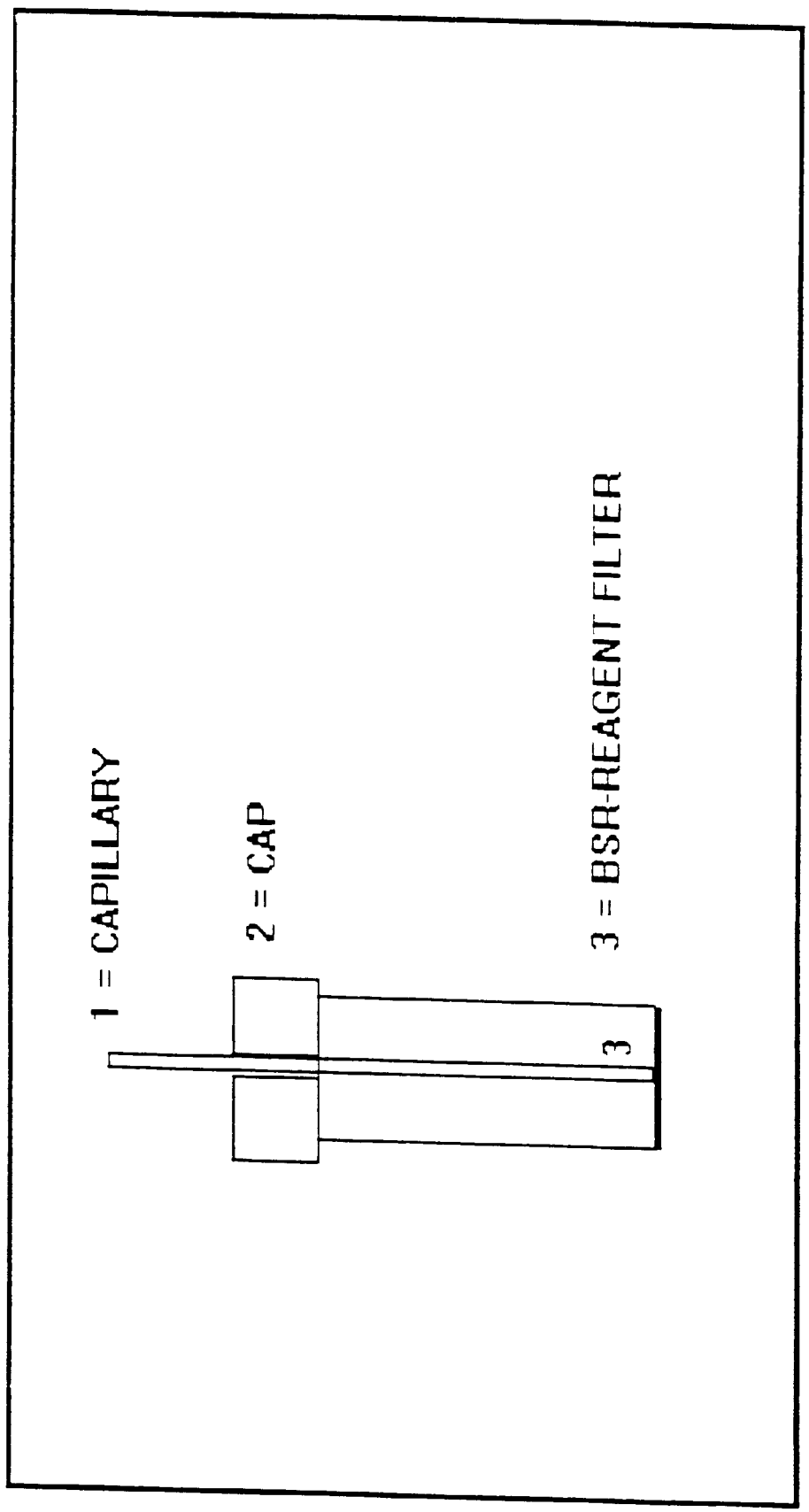
FIG. 4 shows a glass or plastic (acrylic, polystyrene, polypropene etc.) analyzer cuvette composed of a capillary (1), cap (2) and porous membrane disk (3) useful in practising the present invention.

Instead of drying BSR-reagent onto the walls of the cuvette it may also be impregnated and dried into a porous membrane disk on the bottom of a cuvette. The area of the membrane disk used in the Quikread 3 application is 50 mm$^2$. Ten (10) µl of BSR-reagent containing 21 mg/ml of BSR (Lot. UA001) were impregnated and dried into cuvettes containing the porous membrane or filter. FIG. 4 shows the cuvette or tube containing a heparinized sampling capillary tube (1) of stationary volume penetrating the capillary cap (2).

The capillary is filled up with blood by keeping the cuvette at a horizontal position. When the capillary is full the cuvette is turned into an upright position. Then the capillary force of the porous membrane disk (3) empties the capillary. The blood cells precipitate in the membrane disk by the effect of the BSR-reagent. The plasma can be rinsed from the disk by addition of buffer into the cuvette.

EXAMPLES OF THE USE OF BSR-REAGENT

EXAMPLE 1

THE EFFICACY OF THE PRECIPITATION BY USING DIFFERENT BSR-REAGENT APPLICATIONS

The precipitation of blood cells was tested by comparing three different applications i.e. use of soluble BSR-reagent (APPL. 1), BSR-reagent dried onto the wall of the cuvette (APPL. 2), and BSR-reagent impregnated and dried into a porous membrane (APPL. 3). An optimal concentration of BSR-reagent where used in each application. The precipitation efficacy was interpreted by diluting the precipitated blood sample ad 1000 µl with buffer and by determining the absorbance value at a wavelength of A 520 nm with the Quikread 3 analyzer.

TABLE 3

PRECIPITATION EFFICACY OF THE BSR-REAGENT ON SAMPLE BACKGROUND

| TIME (s) | APPL. 1. | APPL. 2. | APPL. 3. |
| --- | --- | --- | --- |
| 0 | 0.117 | 0.011 | 0.024 |
| 20 | 0.117 | 0.011 | 0.021 |
| 40 | 0.112 | 0.011 | 0.022 |
| 60 | 0.109 | 0.012 | 0.023 |
| 80 | 0.109 | 0.010 | 0.024 |
| 100 | 0.110 | 0.010 | 0.024 |
| 120 | 0.107 | 0.011 | 0.024 |
| 140 | 0.105 | 0.011 | 0.024 |
| 160 | 0.107 | 0.011 | 0.023 |
| 180 | 0.106 | 0.012 | 0.023 |

Dry-BSR-reagent (APPL. 2) and membrane-BSR-reagent (APPL. 3) precipitate cells more completely than soluble-BSR-reagent (APPL. 1). The absorbance values are 5–10 times lower in APPL. 2 and 3. Moreover, the absorbance value becomes stable faster (under 20 s) when precipitating with dry-BSR-reagent. When precipitating with soluble BSR-reagent the absorbance may drift for a few minutes.

EXAMPLE 2

HISTOLOGICAL STUDIES OF THE PRECIPITATING EFFICACY OF THE BSR-REAGENT

After precipitation the blood sample (20 µl) was diluted with 1000 µl of buffer, then a sample was taken and stained with chrystal violet and counted in a Burker-chamber under a microscope. The leukocytes and red cells were counted separately in the same sample volume. The soluble-BSR-reagent (APPL. 1) precipitated the cells less effectively than dry-BSR-reagent (APPL. 2) or membrane-BSR-reagent (APPL. 3). The relative proportion of the leukocytes increased 200×. Dry-BSR-reagent (APPL. 2) precipitated all leukocytes, but some red cells could be noticed in the supernatant. The most efficient precipitation was observed with membrane-BSR-reagent (APPL. 3) which precipitated all cells. Precipitating by this method did not either require any vortexing.

TABLE 4

PRECIPITATING EFFICACY OF THE BSR-REAGENT

| | APPL. 1. | APPL. 2. | APPL. 3. |
| --- | --- | --- | --- |
| Vortexing time | 30 s | 10 s | 0 s |
| Incubation time | 210 s | 30 s | 30 s |
| Red cells ×10$^{-3}$/ml | 206 | 7 | 0 |
| Leukocytes ×10$^{-3}$/ml | 40 | 0 | 0 |

EXAMPLE 3

DETERMINATION OF CRP FROM WHOLE BLOOD BY MEANS OF QUIKREAD 3 ANALYZER

Materials:

BSR-reagent cuvettes

Anti-CRP-latex

QR-CRP reaction buffer (Orion Diagnostica)

Measurement application:

Twenty (20) µl of EDTA/heparin blood is pipetted into a round bottom BSR-reagent cuvette. The cells are precipitated either by vortexing or rotating the tube. After the precipitation has occured 1000 µl of reaction buffer is added into the BSR-reagent cuvette. After gentle mixing the sample cuvette is incubated for 3 min in the incubation well (40° C.) of the Quikread 3 analyzer. After incubation the cuvette is transferred into the reading well for background absorbance measurement. Then 50 μl of anti-CRP-reagent is added followed by vortexing and an incubation of 3 minutes before turbidimetric end point measurement.

Figure 5:
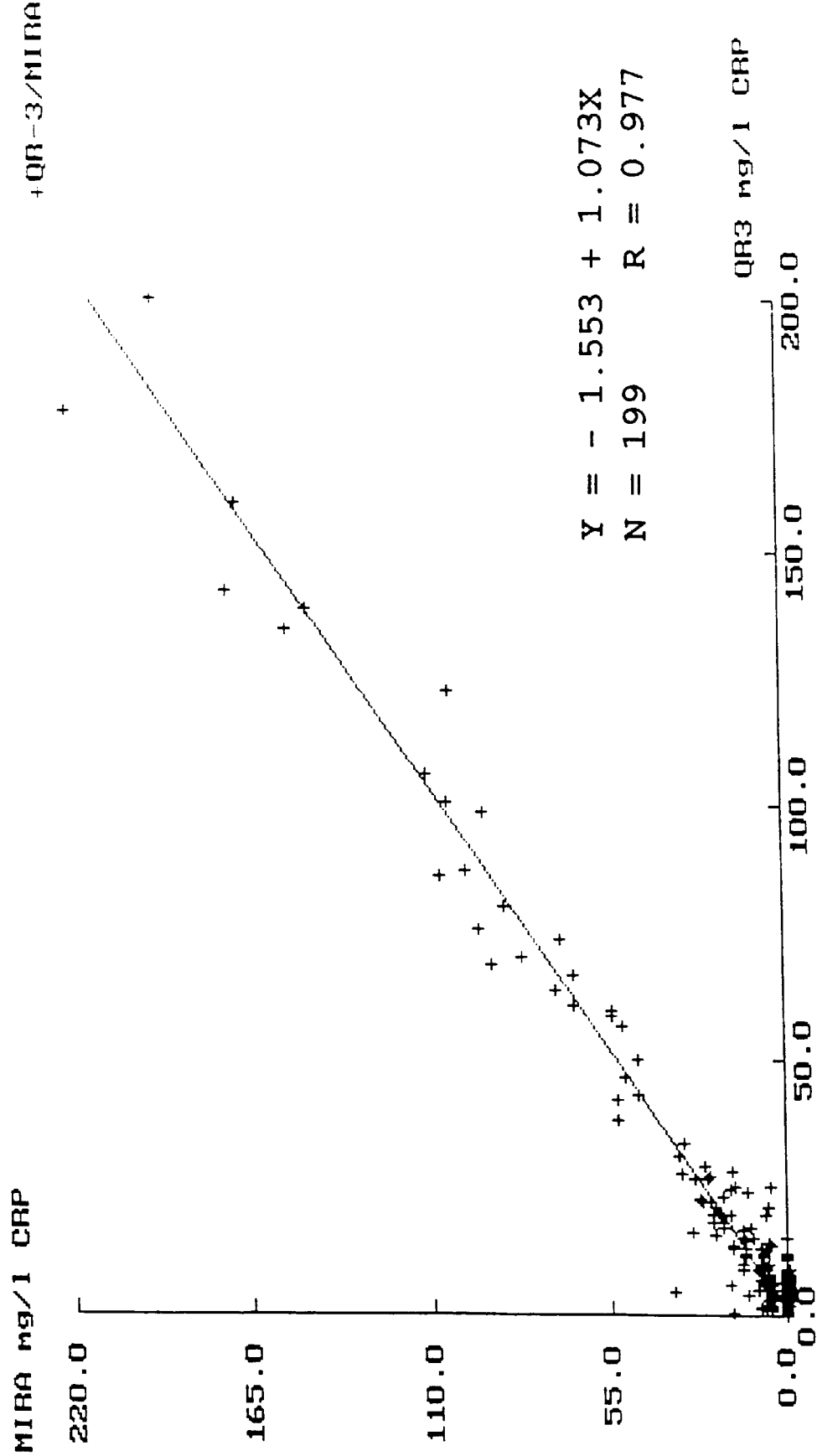
FIG. 5 shows the correlation of the results obtained when CRP-determinations were performed either with Quikread 3 (Orion Diagnostica; X-axis) or with Cobas Mira (Roche Diagnostic System).

FIG. 5 shows the correlation of the results obtained when CRP-determinations were performed either with Quikread 3 (X-axis) or with Cobas Mira. For Quikread 3 determinations whole blood samples and BSR-reagent tubes were used. For Cobas Mira determinations plasma samples, from the same patients as above, and tests applicable for Orion Diagnostica's immunoturbidimetric (IT) method were used.

EXAMPLE 4

WHOLE BLOOD CRP MEASUREMENT WITH TURBOX ANALYZER

Materials:

BSR-reagent cuvettes

CRP antiserum (Orion Diagnostica)

CRP Turbox calibrator (Orion Diagnostica)

Turbox CRP reaction buffer (Orion Diagnostica)

Measurement application:

Fifty (50) μl of EDTA/heparin blood is pipetted into two BSR-reagent cuvettes which fit into the Turbox reading well. The cells are precipitated either by vortexing or rotating the tubes. Five hundred (500) μl of reaction buffer is added to one of the tubes for determination of the sample background. The same volume (500 μl) of antiserum solution is added to the other tube. After incubation for 30 minutes at room temperature the CRP concentration of both tubes was determined in a Turbox analyzer. The apparatus gives the CRP concentration based on a standard curve which has been encoded on a magnetic card.

Table 5 shows the results of Turbox CRP (Orion Diagnostica) determinations by using whole blood samples (50 μl) in BSR-reagent cuvettes and plasma samples (30 μl) in Turbox cuvettes. The blank(BL)-LSU (Light Scattering Unit) values of precipitated whole blood samples were of the same order of magnitude as those obtained with plasma samples from the same patients. In whole blood (50 μl) the portion of plasma was on the average 30 μl. The correlation of the obtained CRP-results when comparing whole blood and plasma samples was good.

TABLE 5

| | WHOLE BLOOD | | PLASMA | |
|---|---|---|---|---|
| SAMPLE | BL-LSU | CRP mg/l | BL-LSU | CRP mg/l |
| 1 | 61 | 50 | 43 | 50 |
| 2 | 75 | <10 | 75 | <10 |
| 3 | 78 | 65 | 285 | 50 |
| 4 | 153 | <10 | 195 | <10 |
| 5 | 71 | <10 | 111 | <10 |
| 6 | 65 | 51 | 61 | 54 |

I claim:

1. An apparatus for determination of an analyte in the plasma fraction of a sample of whole blood, comprising
   a cuvette or tube having a closed bottom portion and inner surfaces; and
   a dried, blood-dissolvable reagent comprising agglutinin extracted from potato, which is dried and dissolvable into a blood sample, wherein said reagent is (a) coated on an inner surface of said cuvette or tube, or (b) dried into a porous membrane disk, said porous membrane disk being disposed within said cuvette or tube, whereby when whole blood is provided to said cuvette or tube and said cuvette or tube is agitated, the dried agglutinin dissolves in the blood resulting in the aggregation of blood components, wherein the aggregates settle to the bottom of the cuvette, without centrifugation, thereby creating a plasma fraction suitable for use in diagnostic tests.

2. The apparatus according to claim 1, wherein the membrane disk in the cuvette or tube is mobile or immobile.

3. The apparatus according to claim 1, which further comprises a heparinized capillary, through which said blood sample can be drawn into said cuvette or tube.

4. The apparatus according to claim 1, wherein said cuvette or tube has dimensions which are suitable for drawing a small blood sample of about 1 μl to about 100 μl.

5. The apparatus according to claim 1, wherein the agglutinin extracted from potato is thermostable agglutinin.

6. The apparatus according to claim 1, wherein the agglutinin extracted from potato is specific for the N-acetyl-D-glucosamin-oligomers, causing agglutination of erythrocytes, leukocytes and thrombocytes.

7. The apparatus according to claim 1, wherein the agglutinin is impure potato agglutinin (BSR), pure STA-lectin or any other lectin which agglutinates cells but does not bind plasma components to be analyzed.

8. The apparatus according to claim 1, wherein the agglutinin is comprised in a specific BSR-reagent.

9. A test kit for the determination of an analyte in the plasma fraction of a sample of whole blood, comprising, in a packaged combination at least one analyzer cuvette or tube according to claim 1.

10. A method for determination of an analyte in the plasma fraction of a sample of whole blood comprising
   providing a whole blood sample to the apparatus according to claim 1, thereby creating a plasma fraction suitable for use in diagnostic tests; and
   determining the analyte in the resulting plasma fraction, without physically removing blood cells from the sample.

11. The method according to claim 10 further comprising agitating the apparatus containing the whole blood sample and allowing the plasma fraction to separate from the blood cells prior to the step of determining.

12. The method according to the claim 10, wherein the blood sample further comprises an anticoagulant.

13. The method according to claim 12, wherein the anti-coagulant is EDTA or heparin.

14. The method according to claim 10, wherein the plasma fraction is used for diagnostic assays.

15. The method according to claim 14, wherein the diagnostic assays are selected from immunometric and colorimetric assays and rapid tests.

16. The method according to claim 15, wherein said rapid test is a strip test.

17. An apparatus for determination of an analyte in the plasma fraction of a sample of whole blood, comprising
   a cuvette or tube having a closed bottom portion and inner surfaces; and
   a dried reagent comprising agglutinin extracted from potato, wherein said reagent is coated on an inner surface of said cuvette or tube or said reagent is dried into a porous membrane disk, said porous membrane disk being disposed within said cuvette or tube, whereby when said tube or cuvette contains whole blood, the agitation of said tube or cuvette results in the aggregation of blood components, wherein said aggregates settle to the bottom of said tube or cuvette, without centrifugation, thereby creating a plasma fraction suitable for use in diagnostic tests.

* * * * *